(12) United States Patent
Xie (10) Patent No.: US 9,550,011 B2
(45) Date of Patent: Jan. 24, 2017

(54) SURFACE COATINGS FOR BIOLOGICAL IMPLANTS AND PROSTHESES

(71) Applicant: INDIANA UNIVERSITY RESEARCH AND TECHNOLOGY CORPORATION, Indianapolis, IN (US)

(72) Inventor: Dong Xie, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 118 days.

(21) Appl. No.: 14/398,181

(22) PCT Filed: May 3, 2013

(86) PCT No.: PCT/US2013/039415
§ 371 (c)(1),
(2) Date: Oct. 31, 2014

(87) PCT Pub. No.: WO2013/166358
PCT Pub. Date: Nov. 7, 2013

(65) Prior Publication Data
US 2015/0109573 A1    Apr. 23, 2015

Related U.S. Application Data

(60) Provisional application No. 61/642,339, filed on May 3, 2012.

(51) Int. Cl.
*G02C 7/00* (2006.01)
*A61L 27/34* (2006.01)
(Continued)

(52) U.S. Cl.
CPC .............. *A61L 27/34* (2013.01); *A61F 2/16* (2013.01); *A61F 2/82* (2013.01); *A61L 27/16* (2013.01);
(Continued)

(58) Field of Classification Search
CPC .......... A61L 27/34; A61L 27/18; A61L 27/16; A61F 2/16; A61F 2/82; G02C 7/049
(Continued)

(56) References Cited

U.S. PATENT DOCUMENTS 5,932,299 A  *  8/1999  Katoot ............................ 427/508
7,247,387 B1 *  7/2007  Huang ............................ 428/447
(Continued)

FOREIGN PATENT DOCUMENTS

WO     2012/035302 A1    3/2012

OTHER PUBLICATIONS

PCT International Search Report and Written Opinion completed by the ISA/US on Jul. 3, 2013 and issued in connection with PCT/US2013/039415.
(Continued)

*Primary Examiner* — James Greece
(74) *Attorney, Agent, or Firm* — Barnes & Thornburg LLP (57) ABSTRACT

A functionalized polymer system is described herein for preparing and/or modifying biological implants and prostheses. In one aspect, the polymer system once applied to the surface of a biological implant or prosthesis, or once used in preparing a biological implant or prosthesis comprises a surface that is more hydrophilic, more wettable, more comfortable, resists cell adhesion, resists protein deposition, or a combination thereof. In one embodiment, a coated biological implant or prosthetic is described herein. The coated biological implant or prosthetic comprises a substrate form-
(Continued)

ing the basic structure of the implant or prosthetic, and a coating comprising a polymer, where the coating is capable of resisting cell adhesion, protein deposition, or a combination thereof.

16 Claims, 4 Drawing Sheets

(51) Int. Cl.
    *A61L 31/10*     (2006.01)
    *A61F 2/16*     (2006.01)
    *A61F 2/82*     (2013.01)
    *A61L 27/16*     (2006.01)
    *A61L 27/18*     (2006.01)
    *G02C 7/04*     (2006.01)

(52) U.S. Cl.
    CPC ............... *A61L 27/18* (2013.01); *A61L 31/10* (2013.01); *G02C 7/049* (2013.01); *A61F 2002/1697* (2013.01); *A61F 2210/0076* (2013.01); *A61F 2240/001* (2013.01); *A61L 2400/10* (2013.01); *A61L 2420/02* (2013.01); *A61L 2420/08* (2013.01); *G02C 2202/16* (2013.01)

(58) Field of Classification Search
    USPC ............ 351/159.02, 159.73, 159.74, 159.75; 623/6.11
    See application file for complete search history.

(56) References Cited

U.S. PATENT DOCUMENTS

| | | |
|---|---|---|
| 2003/0157142 A1 | 8/2003 | Negel et al. |
| 2005/0171596 A1 | 8/2005 | Furst et al. |
| 2008/0114123 A1 | 5/2008 | Tighe et al. |
| 2009/0018575 A1 | 1/2009 | Fortune et al. |
| 2010/0159366 A1 | 6/2010 | Shao-Horn et al. |

OTHER PUBLICATIONS

Thornton, et al. "Enzyme Responsive Polymer Hydrogel Beads" Chemical Communications 5913-5915. 2005. <Retrieved on Jul. 4, 2013 from John Hopkins University> entire document.

Rivas, et al. "Poly (N, N'-dimethylacrylamide-co-acrylic acid): Synthesis, Characterization, and Application for the Removal and Separation of Inorganic Ions in Aqueous Solution." Journal of Applied Polymer Science, 67(1):93-100. 1998 entire document.

* cited by examiner

SURFACE COATINGS FOR BIOLOGICAL IMPLANTS AND PROSTHESES

CROSS-REFERENCE TO RELATED APPLICATIONS

This application is a national stage entry under 35 U.S.C. §371 (b) of international application Ser. No.PCT/US2012/039415 filed May 3, 2013, which claims the benefit under 35 U.S.C. §119(e) of U.S. Provisional Application Ser. No. 61/642,339 filed May 3, 2012, the disclosures of which are expressly incorporated by reference in their emtirety.

TECHNICAL FIELD

The invention described herein pertains to biological prostheses and implants. In particular, the invention described herein pertains to coated biological prostheses and implants that are more hydrophilic, wettable, comfortable, and/or capable of resisting cell adhesion and/or protein deposition.

BACKGROUND AND SUMMARY OF THE INVENTION

A functionalized polymer system is described herein for preparing and/or modifying biological implants and prostheses. In one aspect, the polymer system once applied to the surface of a biological implant or prosthesis, or once used in preparing a biological implant or prosthesis comprises a surface that is more hydrophilic, more wettable, more comfortable, resists cell adhesion, resists protein deposition, or a combination thereof.

In one embodiment, a coated biological implant or prosthetic is described herein. The coated biological implant or prosthetic comprises a substrate forming the basic structure of the implant or prosthetic, and a coating comprising a polymer, where the coating is capable of resisting cell adhesion, protein deposition, or a combination thereof.

In another embodiment, a coated biological implant or prosthetic is described herein. The coated biological implant or prosthetic comprises a substrate forming the basic structure of the implant or prosthetic, and a coating comprising a polymer, where the coating is capable of increasing the hydrophilicity of the coated biological implant or prosthetic compared to the substrate.

In another embodiment, a coated biological implant or prosthetic is described herein. The coated biological implant or prosthetic comprises a substrate forming the basic structure of the implant or prosthetic, and a coating comprising a polymer, where the coating is capable of increasing the wettability of the coated biological implant or prosthetic compared to the substrate.

In another embodiment, a coated biological implant or prosthetic is described herein. The coated biological implant or prosthetic comprises a substrate forming the basic structure of the implant or prosthetic, and a coating comprising a polymer, where the coating is capable of improving the comfort of the coated biological implant or prosthetic compared to the substrate.

In another embodiment, a coated biological implant or prosthetic is described herein. The coated biological implant or prosthetic comprises a substrate forming the basic structure of the implant or prosthetic, and a coating comprising a polymer, where the coating is capable of increasing the hydrophilicity and/or wettability of the coated biological implant or prosthetic compared to the substrate as a function of decreasing the contact angle of an aqueous solution on the coated biological implant or prosthetic compared to the substrate.

In another embodiment, a process for coating an implant or prosthetic is described herein. The process comprises the step of contacting a substrate forming the basic structure of the implant or prosthetic with a solution of a polymer.

In another embodiment, a biological implant or prosthetic is described herein. The biological implant or prosthetic comprises a polymer, where the polymer forms the basic structure of the implant, and once formed, where the polymer displays a surface of the implant or prosthetic that resists cell adhesion, protein deposition, or a combination thereof.

In another embodiment, a biological implant or prosthetic is described herein. The biological implant or prosthetic comprises a polymer, where the polymer forms the basic structure of the implant, and once formed, where the polymer displays a surface of the implant or prosthetic that exhibits a low contact angle with an aqueous solution.

In another embodiment, a coating composition is described herein. The coating composition includes a coating polymer as described herein and a solvent.

DETAILED DESCRIPTION

Illustrative biological implants and prostheses are described herein, including but are not limited to ophthalmologic devices and implants, including but not limited to contact lenses, intraocular lenses, and the like, and cardiovascular medical devices, including but not limited to stents, artificial hearts, artificial heart valves, and the like. Such biological implants and prostheses include a surface that is coated as described herein. Illustratively, the biological implant or prosthesis is a contact lens, and the coating provides for enhanced comfort. Illustratively, the biological implant or prosthesis is an intraocular lense (IOL), and the coating provides for enhanced compatibility. Illustratively, the biological implant or prosthesis is an artificial polymer-composed blood vessel or graft, and the coating provides for enhanced blood compatibility. Illustratively, the biological implant or prosthesis is an artificial stent or other cardiovascular device, and the coating provides for enhanced blood compatibility. Illustrative intraocular lenses include but are not limited to monofocal and multifocal IOLs and phakic intraocular lenses (PIOLs).

A coating polymer composition or system is described herein for preparing and/or modifying medical devices for use with biological tissues and/or fluids. In one aspect, the polymer system once applied to the surface of the device, or once used in preparing the device comprises a surface that resists cell adhesion, protein deposition, or a combination thereof. In another aspect, the coating polymer composition or system once applied to the surface of the device, or once used in preparing the device comprises a surface that increases the wettability or hydrophilicity, or a combination thereof.

Illustrative devices include but are not limited to kidney dialysis machinery and other physiological fluid purification devices. It is appreciated that the devices described herein may decrease the inadvertent loss of certain cells and/or proteins from the biological fluid passed through the kidney dialysis machinery or other physiological fluid purification device.

In one embodiment, the coating polymer is covalently bound to the substrate at its end. In another embodiment, the coating polymer is covalently bound to the substrate at a location other than its end. In another embodiment, the coating polymer is covalently bound to the substrate at a plurality of locations. In another embodiment, the coating is series of two or more layers. In one aspect, the first layer is primarily covalently bound to the substrate and the second layer. In another aspect, the second layer is primarily covalently bound to the first layer and the third layer. In another aspect, the third layer is primarily covalently bound to the second layer and, if present, the fourth layer. Coated substrates are described herein that also include additional analogously bound layers.

In another embodiment, one or more layers are cross-linked. In one aspect, the coating polymer layer is cross-linked after it is covalently bound to the substrate, or other layer. In an alternative aspect, the coating polymer layer is cross-linked before it is covalently bound to the substrate, or other layer.

In another embodiment, the biological implants and prostheses described herein comprise a substrate and a coating. Illustrative substrates include a wide variety of polymers, ceramics, metals, and the like. In another embodiment, the biological implants and prostheses described herein, the substrate is a polymer. Illustrative polymers include, but are not limited to, a wide variety of polyurethanes (PUs), such as ethylene glycol-aromatic diisocyanate polyurethanes, including diphenylmethane diisocyanate (MDI), toluene diisocyanate (TDI), and the like, or ethylene glycol-aliphatic diisocyanate polyurethanes, including hexamethylene diisocyanate (HDI), isophorone diisocyanate (IPDI), and the like. Illustrative polymers include, but not limited to, a wide variety of silicone polyether urethanes (SPUs). Illustrative polymers include, but are not limited to, a wide variety of polyacrylates, such as poly(acrylic acid), poly(methacrylic acid), poly(crotonic acid), and ester, amide, and other derivatives thereof. The substrates also include a plurality of reactive groups capable of forming covalent bonds to the coating polymer, such as, but not limited to, one or more OH, $NH_2$, $CO_2H$, CHO, SH and epoxide groups, and combinations thereof. The reactive groups may be included in composition of the substrate, or may alternatively be grafted or added onto the substrate. For example, polymer substrates comprising polyurethanes or polyacrylates may also comprise additional monomers either at the ends of the polymer forming the substrate, or at one or more locations in the interior of the polymer forming the substrate. Illustrative copolymers that include reactive groups include, but are not limited to, polyurethane polymers that are formed with acrylic acid monomers, and derivatives thereof; poly(methyl methacrylate) polymers that are formed with acrylic acid monomers, and derivatives thereof; and the like. Reactive groups may also be grafted on to exiting substrates. For example, PU or SPU substrates may be treated with reagents that modify a plurality of locations on the polymer forming the substrate to introduce amino groups or derivatives thereof; or carboxylic acid groups, or derivatives thereof; and the like. Illustratively, PU or SPU substrates are treated with diisocyanates, then with diamines or diols or amino alcohols to introduce amino or hydroxyl groups, or derivatives thereof. Alternatively, reactive groups are introduced onto substrates by etching, plasma treatment, corona discharge, and the like.

In another embodiment, the coating polymer is a water soluble and/or solvent soluble cross-linked polymer. Also described herein is a coating composition comprising a water soluble cross-linked polymer, a method for using the water soluble and/or solvent soluble cross-linked polymer, and an article for use as a biological implant or prosthesis made from the water soluble and/or solvent soluble cross-linked polymer. Without being bound y theory, it is believed herein that the use of a water soluble and/or solvent soluble cross-linked polymer as a polymer coating may provide a more consistent and improved coating of the biological implant or prosthesis for enhanced polymer coating thickness and surface wettability.

Any of the coating polymers described herein may be cross-linked to form the water and/or solvent soluble cross-linked coating compositions. Illustrative cross-linking agents include, but are not limited to, diisocyanates for carboxylic acid or hydroxyl group, diamines for —NHS or —COOH groups, and diacarboxylic acids for (—NH or —NRH) groups, and the like. The amount of the difunctional crosslinker incorporated to form such a pre-cross-linked polymer ranges from 0.001% to 10% (by mole) of the synthesized polymer.

Illustrative coatings are formed from coating compositions that comprise a coating polymer. Illustrative coating polymers comprise a wide variety of chemical functionality, including PEGs, PEOs, PVAs, PUs, PAs, PAAs, PMMAs, and PDMSs, and the like. The coating polymers also comprise one or more functional groups capable of forming covalent bonds to the substrate, such as, but not limited to, one or more OH, $NH_2$, $CO_2H$, CHO, SH, epoxide, NHS esters, HOBt esters, cyanuric chloride, and ADH, groups, and combinations thereof. Further illustrative coating polymers comprise a wide variety of cross-linked PEGs, PEOs, PVAs, PUs, PAs, PAAs, PMMAs, and PDMSs, and the like. It is appreciated that the cross-linked coating polymers are advantageously water and/or solvent soluble.

Each of the polymers described herein, including the substrate polymers and coating polymers, may be prepared using conventional processes, such as are described herein, and including but not limited to ATRP, RAFT, anionic/cationic polymerization, free-radical polymerization, or chain transfer polymerization, and the like.

In another embodiment, the coating polymer comprises a poly(N-vinylpyrrolidone) (PVP), poly(N,N-dimethylacrylamide) (PDMAm), poly(N-methyl-N-vinylacetomide) (PMVAm), poly(N-vinylformamide) (PVFm), poly(acrylamide) (PAAm), poly(methacrylamide) (PMAAm), poly(ethylene glycol) (PEG), poly(ethylene oxide) (PEO), PEG acrylate (PEGA), PEG methacrylate (PEGMA), poly(vinyl alcohol) (PVA), poly(acrylic acid) (PAA), sodium poly(acrylic acid) salt (PAANa), potassium poly(acrylic acid) salt (PAAK), poly(isopropyl acrylamide) (PIPAAm), poly(2-methacryloyloxyethyl phosphorylcholine) (PMPC), and the like, and copolymers and terpolymers thereof.

In another embodiment, the coating polymer is a copolymer or terpolymer of any of the foregoing, in any combinations, such as, but not limited to, poly(VP-co-AA-co-AANHS), poly(VP-co-DMAm-co-AANHS), poly(VP-co-MVAm-co-AANHS), poly(DMAm-co-MVAm-co-AANHS), poly(VP-co-MPC-co-AANHS), and the like.

In another embodiment, the polymer systems described herein, including the substrate polymers and coating polymers, may include a variety of architectures, including but not limited to linear, star-shaped, comb-shaped and brush-shaped polymer architectures. Such architectures may also be prepared via advanced ATRP, RAFT, or anionic and cationic polymerizations.

Illustrative functional groups that are included in the coating polymer compositions described herein for modifying the surface of a substrate forming an implant, prosthetic, and/or medical device include but are not limited to $CO_2H$, CHO, $NH_2$, OH, NHS, cyanuric chloride, epoxy, ADH, SH, and the like. These functional groups can react directly, or alternatively in the presence of one or more activating reagents, with a wide variety of reactive groups present on surfaces of the substrate, such as $CO_2H$, CHO, $NH_2$, OH, NHS, cyanuric chloride, epoxy, ADH, and SH groups, and the like. It is to be understood that the functional group on the polymer and the functional group on the surface are matched for their reactivity with one another. Illustrative matching pairs include but are not limited to the following:

The coupling reaction conditions between the surfaces and the polymer systems described herein may be very mild where the reaction temperature is illustratively 10 to 40° C., or ambient temperature, or body temperature. The reaction pH is illustratively in the range between 4.5-9.0, or 6.5-8.0, or near or at physiological pH. The reaction medium is illustratively water or buffer. In one embodiment, no catalysts or additives are required. In another illustrative embodiment, only body or body tissue compatible catalysts or additives are added during the coupling reaction. It is appreciated that the reactions are desirably performed where non-toxic, or low toxicity by-products may be produced concurrently from the coupling reactions. It is to be understood that the functionalized biocompatible polymers described herein may also be referred to as surface polymer brushes or dangling polymers.

In one illustrative embodiment of the invention, a coated biological implant is described herein. The implant includes a substrate forming the basic structure of the implant and a coating comprising a polymer, where the coating resists cell adhesion, protein deposition, or a combination thereof.

In another illustrative embodiment, a coated biological prosthetic is described herein. The prosthetic includes a substrate forming the basic structure of the prosthetic and a coating comprising a polymer, where the coating resists cell adhesion, protein deposition, or a combination thereof.

In another illustrative embodiment, a biological implant comprising a polymer is described, where the polymer forms the basic structure of the implant, and once formed, where the polymer displays a surface of the implant that resists cell adhesion, protein deposition, or a combination thereof.

In another illustrative embodiment, a biological prosthetic comprising a polymer is described, where the polymer forms the basic structure of the prosthetic, and once formed, where the polymer displays a surface of the prosthetic that resists cell adhesion, protein deposition, or a combination thereof.

In another illustrative embodiment, a biological implant comprising a polymer is described, where the polymer forms the basic structure of the implant, and once formed, where the polymer displays a surface of the implant that exhibit higher wettability and/or hydrophilicity compared to the substrate or uncoated implant.

In another illustrative embodiment, a biological prosthetic comprising a polymer is described, where the polymer forms the basic structure of the prosthetic, and once formed, where the polymer displays a surface of the prosthetic that exhibit higher wettability and/or hydrophilicity compared to the substrate or uncoated prosthetic.

In another illustrative embodiment, an implant or prosthetic of any one of the foregoing embodiments is described where the implant or prosthesis is a stent.

In another illustrative embodiment, an implant or prosthetic of any one of the foregoing embodiments is described where the implant or prosthesis is a contact lens.

In another illustrative embodiment, an implant or prosthetic of any one of the foregoing embodiments is described where the implant or prosthesis is an intraocular lens.

In another embodiment, processes for preparing biological implants and prostheses are described. The processes include the step of coating a substrate with a coating polymer described herein, where the substrate forms at least a part of the biological implant or prosthesis that is in contact with a biological tissue. The coating step includes contacting the substrate with a coating composition comprising the coating polymer under reaction conditions that form one or more covalent bonds between the coating polymer and the substrate. In another embodiment, the processes include additional coating steps to prepare multilayered coatings on the substrate. In another embodiment, the processes include coating compositions that have been cross-linked prior to contacting with and forming covalent bonds with the substrate. In another embodiment, the processes include steps where the coating compositions are cross-linked after contacting with and forming covalent bonds with the substrate.

Several illustrative embodiments of the invention are described by the following enumerated clauses:

1. An article for use as a biological implant or prosthetic, the article comprising a substrate, and a coating covalently bonded thereto; where the coating comprises a coating polymer, and where the coating is capable of resisting cell adhesion, protein deposition, or a combination thereof.

2. An article for use as a biological implant or prosthetic, the article comprising a substrate, and a coating covalently bonded thereto; where the coating comprises a coating polymer, and where the coating is capable of increasing the hydrophilicity of the article compared to the substrate.

3. An article for use as a biological implant or prosthetic, the article comprising a substrate, and a coating covalently bonded thereto; where the coating comprises a coating polymer, and where the coating is capable of increasing the wettability of the article compared to the substrate.

4. An article for use as a biological implant or prosthetic, the article comprising a substrate, and a coating covalently bonded thereto; where the coating comprises a coating polymer, and where the coating is capable of increasing the comfort of the article compared to the substrate.

4. The article of any one of the preceding clauses wherein the increasing the hydrophilicity, wettability, or comfort of the article compared to the substrate is a function of decreasing the contact angle of an aqueous solution on the article compared to the substrate.

5. A process for manufacturing an article for use as an implant or prosthetic, the process comprising the step of contacting a substrate with a solution of a coating polymer under conditions where the coating polymer will covalently bond to the substrate.

6. The process of any one of the preceding clauses further comprising the step of contacting the article with a solution of an coating polymer under conditions where the coating polymer will covalently bond to the article.

7. A process for manufacturing an article for use as an implant or prosthetic, the process comprising the steps of:

(a) contacting a substrate with a solution of a coating polymer under conditions where the coating polymer will covalently bond to the substrate to form a first coated substrate;

(b) contacting the first coated substrate from (a) with a solution of a coating polymer under conditions where the coating polymer will covalently bond to the first coated substrate to form a second coated substrate;

(c) contacting the second coated substrate from (b) with a solution of a coating polymer under conditions where the coating polymer will covalently bond to the second coated substrate to form a third coated substrate; and (d) optionally repeating step (c) 1 to 5 times.

8. The process of any one of the preceding clauses wherein the solution of the coating polymer comprises water.

9. The process of any one of the preceding clauses wherein the solution of the coating polymer comprises an aqueous buffer.

10. The process of any one of the preceding clauses wherein the solution of the coating polymer comprises an organic solvent.

11. The process of any one of the preceding clauses wherein the solution of the coating polymer comprises tetrahydrofuran (THF), dioxane, hexane, N,N-dimethylformamide (DMF), and the like, and combinations thereof.

12. The process any one of the preceding clauses wherein the concentration of the coating polymer in the aqueous buffer solution is in the range from about 0.001% to about 50% by weight.

13. The process any one of the preceding clauses wherein the concentration of the coating polymer in the aqueous buffer solution is in the range from about 0.01% to about 50% by weight.

14. The process any one of the preceding clauses wherein the contacting step is performed at a pH in the range from about 1.5 to about 12.5.

15. The process any one of the preceding clauses wherein the contacting step is performed at a pH in the range from about 2.9 to about 11.9.

16. The process any one of the preceding clauses wherein the contacting step is performed at a pH in the range from about 2.95 to about 11.95.

17. The process any one of the preceding clauses wherein the contacting step is performed at a pH in the range from about 3 to about 11.

18. The process any one of the preceding clauses wherein the contacting step is performed at a pH in the range from about 5 to about 9.

19. The process any one of the preceding clauses wherein the contacting step is performed at a pH in the range from about 7 to about 8.5.

20. The process any one of the preceding clauses wherein the contacting step is performed at a pH in the range from about 8 to about 8.5.

21. The process any one of the preceding clauses wherein the contacting step is performed at a pH of about 8.

22. The process any one of the preceding clauses wherein the contacting step is performed at a reaction temperature in the range from about 4° C. to about 140° C.

23. The process any one of the preceding clauses wherein the contacting step is performed for a reaction time in the range from about 0.5 min to about 72 h.

24. The process any one of the preceding clauses wherein the contacting step is performed for a reaction time in the range from about 0.5 min to about 48 h.

25. The article or process of any one of the preceding clauses wherein the substrate forms the basic structure of the implant or prosthetic.

26. The article or process of any one of the preceding clauses wherein the biological implant or prosthetic consists essentially of the substrate and the coating.

27. The article or process of any one of the preceding clauses wherein the substrate is a polymer, ceramic, glass, metal, or alloys, or a combination thereof.

28. The article or process of any one of the preceding clauses wherein the substrate is a polymer.

29 The article or process of any one of the preceding clauses wherein the substrate comprises a polyurethane (PU), a silicone polyether urethane (SPU), a polyacrylate, or a copolymer thereof.

30. The article or process of any one of the preceding clauses wherein the substrate comprises a polyacrylate, such as a copolymer of methyl methacrylate and one or more amino-containing monomers, such as N-amino-poly(ethylene glycol) acrylamide, N-amino-poly(ethylene glycol) methacrylamide, N-amino-siloxane-containing acrylamide, N-amino-siloxane-containing methacrylamide, N-amino-alkyl(aryl) acrylamide, N-amino-alkyl(aryl) methacrylamide, and combinations thereof.

31. The article or process of any one of the preceding clauses wherein the substrate comprises a cross-linked polymer network of one or more amino-containing monomers, such as N-amino-poly(ethylene glycol) acrylamides, such as N-amino-poly(ethylene glycol) (meth)acrylamide, N-amino-poly(ethylene glycol) methacrylamide, and the like, N-amino-siloxane-containing acrylamides, such as N-amino-siloxane-containing acrylamide, N-amino-siloxane-containing methacrylamide, and the like, N-amino-alkyl(aryl) acrylamides, such as N-amino-alkyl(aryl)acrylamide, N-amino-alkyl(aryl) methacrylamide, and the like, and combinations thereof, or other substrates that are common for contact lenses and/or IOLs.

32. The article or process of any one of the preceding clauses wherein the substrate comprises a polysiloxane or silicone or silicone-containing crosslinked polymer network comprising a crosslinker, one or more polysiloxanes or silicone monomers, such as are common for contact lenses and/or IOLs, and one or more amino-containing monomers, such as N-amino-poly(ethylene glycol) acrylamide, N-amino-poly(ethylene glycol) methacrylamide, N-amino-siloxane-containing acrylamide, N-amino-siloxane-containing methacrylamide, N-amino-alkyl(aryl) acrylamide, N-amino-alkyl(aryl) methacrylamide, and combinations thereof.

33. The article or process of any one of the preceding clauses wherein the substrate includes one or more reactive groups selected from the group consisting of OH, NHS, $NH_2$, $CO_2H$, CHO, SH and epoxide, or salts thereof.

34. The article or process of any one of the preceding clauses wherein the substrate includes one or more reactive groups selected from the group consisting of OH, $NH_2$, $CO_2H$, and CHO, or salts thereof.

35. The article or process of any one of the preceding clauses wherein the substrate includes one or more reactive groups selected from the group consisting of OH, $NH_2$, and $CO_2H$, or salts thereof.

36. The article or process of any one of the preceding clauses wherein the substrate includes a population of $NH_2$ groups.

37. The article or process of any one of the preceding clauses wherein a surface of the substrate includes a population of amines or amino groups, including primary amino groups, secondary amino groups, or a combination thereof, or salts thereof.

38. The article or process of any one of the preceding clauses wherein the substrate includes a population of $CO_2H$ groups, or salts or activated esters thereof.

39. The article or process of any one of the preceding clauses wherein a surface of the substrate is modified via a chemical reaction to include a population of amines or amino groups, including primary amino groups, secondary amino groups, or a combination thereof, or salts thereof.

40. The article or process of any one of the preceding clauses wherein a surface of the substrate is modified via a chemical reaction to include a population of $CO_2H$ groups, or salts or activated esters thereof.

41. The article or process of any one of the preceding clauses wherein a surface of the substrate is modified via plasma treatment, electron beam, gamma-irradiation or other physical method to include a population of amines or amino groups, including primary amino groups, secondary amino groups, or a combination thereof, or salts thereof.

42. The article or process of any one of the preceding clauses wherein a surface of the substrate is modified via plasma treatment, electron beam, gamma-irradiation or other physical method to include a population of $CO_2H$ groups.

43. A coating polymer composition comprising a water soluble or solvent soluble polymer that includes one or more functional groups capable of reacting with the substrate of any one of the preceding clauses.

44. The article or process or coating polymer composition of any one of the preceding clauses wherein the coating polymer is a random copolymer or a random terpolymer.

45. The article or process or coating polymer composition of any one of the preceding clauses wherein the coating polymer comprises a poly(N-vinylpyrrolidone), poly(N,N-dimethylacrylamide), poly(N-methyl-N-vinylacetamide), poly(N-vinylformamide), poly(acrylamide), poly(methacrylamide), poly(ethylene glycol), poly(ethylene oxide), poly(isopropyl acrylamide), poly(2-methacryloyloxy)ethyl)dimethyl-(3-sulfopropyl)ammonium hydroxide, poly(2-acryloyloxy)ethyl)dimethyl-(3-sulfopropyl)ammonium hydroxide), or phosphocoline-containing polymer, such as poly(methacryloyl phosphorylcholine), or a copolymer or terpolymer thereof, and one or more functional groups capable of forming a covalent bond with the substrate reactive group.

46. The article or process or coating polymer composition of any one of the preceding clauses wherein the coating polymer comprises a poly(N-vinylpyrrolidone), poly(N,N-dimethylacrylamide), poly(N-methyl-N-vinylacetamide), poly(acrylamide), poly(methacrylamide), poly(N-vinylformamide), or poly(methacryloyl phosphorylcholine), or a copolymer or terpolymer thereof, and one or more functional groups capable of forming a covalent bond with the substrate reactive group.

47. The article or process or coating polymer composition of any one of the preceding clauses wherein the coating polymer comprises a poly(N-vinylpyrrolidone) and one or more functional groups capable of forming a covalent bond with the substrate reactive group.

48. The article or process or coating polymer composition of any one of the preceding clauses wherein the coating polymer comprises a poly(N,N-dimethylacrylamide), poly(acrylamide), poly(methacrylamide), or poly(methacryloyl phosphorylcholine), or a copolymer or terpolymer thereof, and one or more functional groups capable of forming a covalent bond with the substrate reactive group.

49. The article or process or coating polymer composition of any one of the preceding clauses wherein the coating polymer comprises a copolymer of (a) (N-vinylpyrrolidone), (N,N-dimethylacrylamide), (N-methyl-N-vinylacetamide), (N-vinylformamide), (acrylamide), (methacrylamide), (ethylene glycol), (isopropyl acrylamide), (methacryloyl phosphorylcholine), or (ethylene oxide), or a combination thereof; and (b) PEG acrylate, PEG methacrylate, (vinyl alcohol), (acrylic acid), (acrylic acid) sodium salt, poly(hydroxylethylmethacrylate), poly(hydroxylethylacrylate), poly(styrene sulfonic acid) and sodium and potassium salts thereof, poly(glycidyl methacrylate), poly(glycidyl acrylate), or (acrylic acid) potassium salt, alginic acid, hyaluronic acid, heparin, dextran, or a combination thereof.

50. The article or process or coating polymer composition of any one of the preceding clauses wherein the coating polymer comprises a poly(N-vinylpyrrolidone-acrylic acid), poly(VP-AA-AANHS), poly(VP-DMAm-AANHS), poly(VP-MVAm-AANHS), poly(DMAm-MVAm-AANHS), poly(VP-MPC-AANHS), or salt of any of the foregoing, and combinations thereof.

51. The article or process or coating polymer composition of any one of the preceding clauses wherein the coating polymer comprises a poly(VP-AA), poly(VP-DMAm-AA), poly(VP-MVAm-AA), poly(DMAm-MVAm-AA), poly(VP-MPC-AA), or salt of any of the foregoing, and combinations thereof; where at least a portion of the acrylic acid monomers are activated esters.

52. The article or process or coating polymer composition of any one of the preceding clauses wherein substantially all of the acrylic acid monomers are activated esters.

53. The article or process or coating polymer composition of any one of the preceding clauses wherein all of the acrylic acid monomers are activated esters.

54. The article or process or coating polymer composition of any one of the preceding clauses wherein the activated esters are NHS or HOBt esters, or a combination thereof.

55. The article or process or coating polymer composition of any one of the preceding clauses wherein the coating polymer comprises a poly(VP-AANHS), poly(VP-DMAm-AANHS), poly(VP-MVAm-AANHS), poly(DMAm-MVAm-AANHS), poly(VP-MPC-AANHS).

56. The article or process or coating polymer composition of any one of the preceding clauses wherein the coating polymer includes one or more functional groups capable of reacting with an amino, or a carboxylic acid group on the surface of the substrate.

57. The article or process or coating polymer composition of any one of the preceding clauses wherein the one or more functional groups are selected from OH, $NH_2$, NHR, $CO_2H$, CHO, SH and epoxide, optionally substituted CO2-(N-hydroxysuccinimide), optionally substituted CO2-(N-hydroxybenzotriazole), C(OR)=NH, NCO, chlorotriazine, $H_2NNH$, and $H_2NNHC(O)(CH_2)_nC(O)NHNH$, where R is independently in each instance selected from alkyl, aryl, and arylalkyl, each of which is optionally substituted, and where n is an integer from 1 to about 8.

58. The article or process or coating polymer composition of any one of the preceding clauses wherein the coating polymer includes one or more functional groups selected from the group consisting of epoxide, amine, hydroxyl, N-hydroxysuccinimide, cyanuric chloride, ADH, and thiol.

59. The article or process or coating polymer composition of any one of the preceding clauses wherein the substrate includes a plurality of amino groups and the coating polymer includes one or more succinimide ester (SE), carboxyl, maleimide, or imidoester functional groups, or a combination thereof.

60. The article or process or coating polymer composition of any one of the preceding clauses wherein the one or more functional groups include N-hydroxy succinimide ester groups.

61. The article or process or coating polymer composition of any one of the preceding clauses wherein the one or more functional groups include maleimide groups.

62. The article or process or coating polymer composition of any one of the preceding clauses wherein the one or more functional groups include imidoester groups.

63. The article or process or coating polymer composition of any one of the preceding clauses wherein the one or more functional groups include carboxyl groups.

64. The article or process or coating polymer composition of any one of the preceding clauses wherein the one or more functional groups include amino groups, including primary amino and/or secondary amino groups.

65. The article or process or coating polymer composition of any one of the preceding clauses wherein the coating polymer includes a functional group at each end.

66. The article or process or coating polymer composition of any one of the preceding clauses wherein the coating polymer includes a plurality of functional groups at monomer residues along the polymer chain.

67. The article or process or coating polymer composition of any one of the preceding clauses wherein the coating polymer is a cross-linked water soluble polymer.

68. The article or process or coating polymer composition of any one of the preceding clauses wherein the coating polymer is an amide cross-linked water soluble polymer 69. The article or process or coating polymer composition of any one of the preceding clauses wherein the coating polymer is a P(VP-AA) copolymer cross-linked with PVP-NH2.

70. The article or process or coating polymer composition of any one of the preceding clauses wherein the coating polymer is a P(DMAm-AA) copolymer cross-linked with PVP-NH2.

71. The article or process or coating polymer composition of any one of the preceding clauses wherein the coating polymer is a P(MVAm-AA) copolymer cross-linked with PVP-NH2.

72. The article or process or coating polymer composition of any one of the preceding clauses wherein the cross-linked water soluble polymer is about 0.001% to about 10% cross-linked.

73. The article or process or coating polymer composition of any one of the preceding clauses wherein the cross-linked water soluble polymer is about 0.001% to about 5% cross-linked.

74. The article or process or coating polymer composition of any one of the preceding clauses wherein the cross-linked water soluble polymer is about 0.001% to about 3% cross-linked.

75. The article or process or coating polymer composition of any one of the preceding clauses wherein the cross-linked water soluble polymer is about 0.001% to about 2% cross-linked.

76. The article or process or coating polymer composition of any one of the preceding clauses wherein the cross-linked water soluble polymer has a number average molecular weight in the range from about 100,000 to about 1,000,000.

77. The article or process or coating polymer composition of any one of the preceding clauses wherein the cross-linked water soluble polymer has a weight average molecular weight in the range from about 50,000 to about 500,000.

78. The article or process or coating polymer composition of any one of the preceding clauses wherein the coating polymer has a weight average molecular weight in the range from about 1,000 to about 1,000,000.

79. The article or process or coating polymer composition of any one of the preceding clauses wherein the coating polymer has a weight average molecular weight in the range from about 1,000 to about 600,000.

80. The article or process or coating polymer composition of any one of the preceding clauses wherein the coating polymer has a weight average molecular weight in the range from about 100,000 to about 1,000,000.

81. The article or process or coating polymer composition of any one of the preceding clauses wherein the coating polymer has a weight average molecular weight in the range from about 2,000 to about 500,000.

82. The article or process or coating polymer composition of any one of the preceding clauses wherein the coating polymer has a weight average molecular weight in the range from about 5,000 to about 500,000.

83. The article or process or coating polymer composition of any one of the preceding clauses wherein the coating polymer has a weight average molecular weight in the range from about 5,000 to about 120,000.

84. The article or process or coating polymer composition of any one of the preceding clauses wherein the coating polymer has a number average molecular weight in the range from about 800 to about 500,000.

85. The article or process or coating polymer composition of any one of the preceding clauses wherein the coating polymer has a number average molecular weight in the range from about 800 to about 300,000.

86. The article or process or coating polymer composition of any one of the preceding clauses wherein the molar ratio of monomer residues that do not have a functional group to monomer residues that include a functional group is in the range from about 99.9 to about 25.5.

87. The article or process or coating polymer composition of any one of the preceding clauses wherein the molar ratio of monomer residues that do not have a functional group to monomer residues that include a functional group is in the range from about 99.5 to about 25.5.

88. The article or process or coating polymer composition of any one of the preceding clauses wherein the molar ratio of monomer residues that do not have a functional group to monomer residues that include a functional group is in the range from about 99.9 to about 35.

89. The article or process or coating polymer composition of any one of the preceding clauses wherein the molar ratio of monomer residues that do not have a functional group to monomer residues that include a functional group is in the range from about 99 to about 65.

90. The article or process or coating polymer composition of any one of the preceding clauses wherein the molar ratio of monomer residues that do not have a functional group to monomer residues that include a functional group is in the range from about 97 to about 65.

91. The article or process or coating polymer composition of any one of the preceding clauses wherein the molar ratio of monomer residues that do not have a functional group to monomer residues that include a functional group is in the range from about 99 to about 80.

92. The article or process or coating polymer composition of any one of the preceding clauses wherein the molar ratio of monomer residues that do not have a functional group to monomer residues that include a functional group is in the range from about 95 to about 80.

93. The article or process of any one of the preceding clauses wherein the implant or prosthesis is a stent.

94. The article or process of any one of the preceding clauses wherein the implant or prosthesis is a contact lens.

95. The article or process of any one of the preceding clauses wherein the implant or prosthesis is an intraocular lens.

In reciting the foregoing collection of clauses, it is to be understood that all possible combinations of features, and all possible subgenera and sub-combinations are described.

Illustrative organic solvents include, but are not limited to, tetrahydrofuran (THF), dioxane, hexane, N,N-dimethylformamide (DMF), and the like,

It is to be understood that the term "polyacrylate" as used herein generally refers to any polymer of an acrylic acid or analog or derivative thereof. Illustratively, the polyacrylate is a polymer of acrylic acid, methacrylic acid, crotonic acid, or a salt, an ester, or amide derivative of any of the foregoing, or a combination thereof.

In another embodiment, the coating polymer is a random copolymer or a random terpolymer. It is to be understood that a random copolymer or a random terpolymer may differ from a block copolymer or block terpolymer and does not have a predetermined pattern of monomers. Instead, the monomers may be in any number of patterns, including a statistical distribution based on the relative mole ratio.

Illustratively, the coating polymer comprises the formulae:

or or where A and A' in each instance are each independently selected from NVP, DMAm, MVAm, VFm, AAm, MAAm, PEG, PEO, PEGA, PEGMA, PVA, AA, AANa, AAK, IPAAm, and MPC, and combinations thereof;

B in each instance is an independently selected vinyl monomer that includes a carboxylic acid or derivative thereof, including activated esters capable of forming covalent bonds with reactive groups on a substrate, or an amino or derivative thereof capable of forming covalent bonds with reactive groups on a substrate;

C is in each instance is an independently selected vinyl monomer that includes a carboxylic acid or salt thereof;

n in each instance is an independently selected integer; and x, y, and z, in each instance are each independently selected integers, where the ratio of the aggregate x to the aggregate y is in the range from about 99.9/0.1 to about 25.5/74.5;

where the weight average molecular weight of the coating polymer is in the range from about 1,000 to about 1,000,000.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "carboxylic acid and derivatives thereof" includes the group $CO_2H$ and salts thereof, and esters and amides thereof, and CN.

As used herein, the term "sulfonic acid or a derivative thereof" includes $SO_3H$ and salts thereof, and esters and amides thereof.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

As used herein, the term "treating", "contacting" or "reacting" when referring to a chemical reaction generally means to add or mix two or more reagents under appropriate conditions to produce the indicated and/or the desired product. It is to be understood that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

EXAMPLES

Substrate Example 1

Amino-modified Polyurethane. Thermoplastic polyurethane (PU) was dissolved in a mixed solvent with THF/dioxane (2/1) and the formed polymer solution was poured into a petri dish made of Teflon. The dish was conditioned in an oven at room temperature overnight, followed by conditioning at 40° C. for 4 h and at 60° C. overnight. After the PU film (0.5 mm in thickness) was peeled off from the dish and cut into small pieces (6 mm in diameter), these pieces were placed into a flask containing diisocyanatohexane (DIH, 30 part), dibutyltin dilaurate (DBTL, 0.1 part) and hexane (300 part). The reaction was run at 50° C. for 2 h, followed by washing with hexane and ether numerous times. The activated PU films having NCO were then immediately immersed in a flask containing ethylene diamine (EDA), DBTL and ether. The reaction was refluxed at 50° C. for 4 h, following by washing with ether several times.

Substrate Example 2

Amino-modified Silicone Polyether Urethane. Thermoplastic silicone polyether urethane (SPU) was surface-modified with active amine following the exact procedures as described in Substrate Example 1.

Substrate Example 3

Amino-modified Polymethacrylate. To a solution containing acrylaloyl chloride (25 parts) and THF at 0° C., diaminopoly(ethylene glycol) (PEG, Mw=400, 50 parts) and triethylamine (15 parts) was added dropwise. After additional 6 h reaction at room temperature, N-amino-PEG-acrylamide was obtained by rotary evaporation. To a solution of methyl methacrylate (70 parts) and N-amino-PEG-acrylamide (30 parts) in N,N-dimethylformamide (DMF, 300 parts), 2,2'-azobisisobutyronitrile (AIBN, 1 part) was added. The reaction was run under $N_2$ purging at 65-70° C. for 8 h. Then the solution was poured into a petri dish to cast a membrane. The polymer in petri dish was dried in an oven at 70° C. overnight and then at 150° C. for additional two hours.

Substrate Example 4

Amino-modified Crosslinked Silicone Contact lenses. N,N-Dimethylacrylamide (DMAm) (50 parts), 3-[tris(trimethylsiloxy)silyl]propyl methacrylate (37 parts), ethylene glycol dimethacrylate (1 part), N-amino-PEG-acrylamide (10 parts, see Example 4), and Irgacure 184 were mixed to form a uniform liquid solution. The liquid was placed into two pieces of transparent glass slide, followed by UV photo-cured for 5 min via a UV light unit. The cured transparent polymer film (equivalent to contact lenses) was taken out and used for functional PVP coating.

Coating Polymer Example 5

Poly(VP-AA) with multi-point acrylic acid Functional Groups. To a solution of acrylic acid (AA, 40 parts) and N-vinylpyrrolidone (NVP, 550 parts) in water (1500 parts), potassium persulfate (6 parts) was added. The reaction was run under $N_2$ purging at 95° C. for 8 h, followed by freeze drying and storing prior to use.

Coating Polymer Example 6

Poly(VP-AA) with multi-point acrylic acid functional groups. To a solution of AA (4 parts) and NVP (146 parts) in DMF (400 parts), AIBN (2.3 parts) was added. The reaction was run under $N_2$ purging at 65-70° C. for 6 h, followed by precipitation with diethyl ether, drying in vacuum and storing prior to use.

Coating Polymer Example 7

Poly(VP) with end-capped with acid functional groups. To a solution of NVP (50 parts) in DMF (140 parts), AIBN (0.2 parts) and mercaptoacetic acid (MAA, 2.5 parts) were added. The reaction was run under $N_2$ purging at 65-70° C. for 6 h, followed by precipitation with diethyl ether, drying in vacuum and storing prior to use.

Coating Polymer Example 8

Poly(VP-AANHS) with multi-point NHS functional groups. To a solution of the polymer (15 parts) synthesized from Example 6 in DMF (60 parts), NHS (1 part) and 1-Ethyl-3-(3-dimethylaminopropyl) carbodiimide hydrochloride (EDC, 1.7 parts) were added, the reaction was run at room temperature overnight. After the precipitates were filtered out, the polymer was precipitated from DMF with diethyl ether, followed by drying in a vacuum oven.

Coating Polymer Example 9

Poly(VP-AANHS) with multi-point NHS functional groups. To a solution of the polymer (15 parts) synthesized from Example 5 in DMF (60 parts), NHS (1 part) and N,N'-dicyclohexylcarbodiimide (DCC, 1.6 parts) were added, the reaction was run at room temperature overnight. After the precipitates were filtered out, the polymer was precipitated with diethyl ether, followed by drying in a vacuum oven.

Coating Polymer Example 10

Poly(VP-AANHS). The polymers from Examples 5 and 7 were functionalized with NHS similarly to those described in Examples 8 and 9.

Coating Polymer Example 11

Poly(VP-AANHS), One-pot synthesis with multi-point NHS functional groups. To a solution of AA (4 parts) and NVP (146 parts) in DMF (400 parts), AIBN (1.5 parts) was added. The reaction was run under $N_2$ purging at 65-70° C. for 6 h, followed by cooling down to room temperature (RT). After addition of NHS (10 parts), pyridine (1 part) and DCC (16 parts), the reaction was run at RT overnight. After the precipitates were filtered out, the polymer was precipitated with diethyl ether, followed by drying in a vacuum oven.

Coating Polymer Example 12

Poly(VP) end-capped with AANHS, One-pot synthesis with end-capped with NHS functional groups. To a solution of NVP (50 parts) in DMF (140 parts), AIBN (0.2 parts) and MAA (2.5 parts) were added. The reaction was run under $N_2$ purging at 65-70° C. for 6 h, followed by cooling down to room temperature (RT). After addition of NHS (8 parts), pyridine (1 part) and DCC (16 parts), the reaction was run at RT overnight. After the precipitates were filtered out, the polymer was precipitated with diethyl ether, followed by drying in a vacuum oven.

Coating Polymer Example 13

Crosslinked water-soluble poly(VP-AANHS), One-pot synthesis of prepolymer with multi-point NHS functional groups. To a solution of AA (4 parts) and NVP (146 parts) in DMF (400 parts), AIBN (1.5 parts) was added. The reaction was run under $N_2$ purging at 65-70° C. for 6 h, followed by cooling down to room temperature (RT). After addition of NHS (10 parts), hexamethylenediamine (1.6 parts), pyridine (1 part) and DCC (20 parts), the reaction was run at RT overnight. After the precipitates were filtered out, the polymer was precipitated with diethyl ether, followed by drying in a vacuum oven.

Coating Polymer Example 14

Crosslinked water-soluble poly(VP-AANHS), Alternative one-pot synthesis of prepolymer with multi-point NHS functional groups. To a solution of AA (4 parts) and NVP (146 parts) in DMF (400 parts), AIBN (1.5 parts) was added. The reaction was run under $N_2$ purging at 65-70° C. for 6 h, followed by adding diisocyanatohexane (1 part) and dibutyltin dilaurate (0.05 part) for additional 3 h reaction. After cooling down to room temperature (RT), followed by addition of NHS (10 parts), pyridine (1 part) and DCC (20 parts), the reaction was run at RT overnight. After the precipitates were filtered out, the polymer was precipitated with diethyl ether, followed by drying in a vacuum oven.

Coating Polymer Example 15

Crosslinked water-soluble poly(DMAm-AANHS) with multi-point NHS functional groups. To a solution of AA (2 parts) and N,N'-Dimethylacrylamide (DMAm, 58 parts) in DMF (180 parts), AIBN (1 part) was added. The reaction was run under $N_2$ purging at 65-70° C. for 6 h, followed by cooling down to room temperature (RT). After addition of NHS (4 parts), pyridine (1 part) and DCC (7 parts), the reaction was run at RT overnight. After the precipitates were filtered out, the polymer was precipitated from DMF with diethyl ether, followed by drying in a vacuum oven.

Coating Polymer Example 16

Poly(MVAm-AANHS) with multi-point NHS functional groups. To a solution of AA (2 parts) and N-Methyl-N-vinylacetamide (MVAm, 58 parts) in DMF (180 parts), AIBN (1 part) was added. The reaction was run under $N_2$ purging at 65-70° C. for 6 h, followed by cooling down to room temperature (RT). After addition of NHS (4 parts), pyridine (1 part) and DCC (7 parts), the reaction was run at RT overnight. After the precipitates were filtered out, the polymer was precipitated from DMF with diethyl ether, followed by drying in a vacuum oven.

Coating Polymer Example 17

Poly(VP-AA-AANHS) with multi-point NHS functional groups. To a solution of AA (13 parts) and NVP (47 parts)

in DMF (200 parts), AIBN (1 part) was added. The reaction was run under $N_2$ purging at 65-70° C. for 6 h, followed by cooling down to room temperature (RT). After addition of NHS (8 parts), pyridine (1 part) and DCC (14 parts), the reaction was run at RT overnight. After the precipitates were filtered out, the polymer containing NVP, AA and NHS, i.e., P(VP-co-AA-co-AANHS) was precipitated with diethyl ether, followed by drying in a vacuum oven.

Coating Polymer Example 18

Poly(VP-AANHS) with multi-point NHS functional groups via AANHS. To a solution of acrylic acid N-hydroxysuccinimide ester (AANHS, 5 parts) and NVP (55 parts) in DMF (200 parts), AIBN (0.9 parts) was added. The reaction was run under $N_2$ purging at 65-70° C. for 6 h, followed by precipitation with diethyl ether, drying in vacuum and storing prior to use.

Coating Polymer Example 19

Poly(VP-AA-AANHS) with multi-point NHS functional groups via AANHS. To a solution of AA (5 parts), AANHS (6 parts) and NVP (29 parts) in DMF, AIBN (1 part) was added. The reaction was run under $N_2$ purging at 65-70° C. for 6 h, followed by precipitating with diethyl ether and drying in a vacuum oven.

Coating Polymer Example 20

PEG end-capped with AANHS. To a solution of poly (ethylene glycol) methyl ether ($M_n$=2000) (PEG, 100 parts) in tetrahydrofuran (THF, 300 parts), succinic anhydride (5 parts) and pyridine (0.1 parts) were added. The reaction was run at 50° C. overnight, followed by precipitation with diethyl ether and drying in vacuum. The purified PEG succinate was further used to react with NHS (6 parts) in THF (400 parts) in the presence of DCC (12 parts) at RT for 6 h. After the precipitates were filtered out, the NHS-containing PEG polymer was precipitated using diethyl ether, followed by drying in a vacuum oven.

Coating Polymer Example 21

Poly(VP-MPC-AANHS) with multi-point NHS functional groups. To a solution of 2-methacryloyloxyethyl phosphorylcholine (MPC, 10 parts), AANHS (2 parts) and NVP (28 parts) in DMF (140 parts), AIBN (1 part) was added. The reaction was run under $N_2$ purging at 65-70° C. for 6 h, followed by precipitating with diethyl ether and drying in a vacuum oven.

Coating Polymer Example 22

PVP end-capped with $NH_2$. To a solution of N-(2-aminoethyl) methacrylamide hydrochloride (20 parts) and NVP (180 parts) in water (500 parts), potassium persulfate (3 parts) was added. The reaction was run under $N_2$ purging at 95° C. for 8 h. Then sodium hydroxide was added to remove hydrochloride to make PVP with available pendent amino groups, followed by dialysis against DI-water and freeze-drying before use.

Example 23

Complex or gel formation test between NHS-containing polymer and $NH_2$-containing polymer. To a container containing P(VP-AANHS) in a buffer solution (pH=8.0), the amino-containing PVP (PVP-$NH_2$ was added and mixed thoroughly. After 10-30 sec, the transparent gel was formed, indicating that PVP-NHS and PVP-$NH_2$ are very reactive and able to form a gel almost instantly. Other NHS-containing polymers showed the same trends as PVP-NHS. The results are shown in Table 1

TABLE 1

| Gel formation[1] of different polymers containing NHS | | |
|---|---|---|
| Material[2] | NHS-content (mole) | Gel time |
| PVP-NHS | 5% | 15 min |
| PVP-NHS | 10% | 2 min |
| PVP-NHS | 15% | 1 min |
| PVP-NHS | 20% | 0.3 min |
| PDMAm-NHS | 5% | 18 min |
| PMVAm-NHS | 5% | 16 min |

[1]PVP-$NH_2$ was mixed with the polymers containing NHS in the presence of water, where pH = 8.5 and Temperature = RT;
[2]PDMAm-NHS = poly(N,N-dimethylacrylamide) with pendent NHS and PMVAm-NHS = poly(N-methyl-N-vinylacetomide with pendent NHS.

Article Example 24

Surface modification with PVP with multi-point AA. To a container containing PVP with multi-point AA in a buffer solution (pH=4.5), the amino-containing PU films and EDC were added. After the reaction was run at room temperature for 3 h, the films were washed with distilled water several times prior to evaluation.

Article Example 25

Surface modification with PVP end-capped with acid groups. To a container containing PVP end-capped with acid groups in a buffer solution (pH=4.5), the amino-containing PU films and EDC were added. After the reaction was run at room temperature for 3 h, the films were washed with distilled water several times prior to evaluation.

Article Example 26

Surface modification with PVP with multi-point NHS. To a container containing PVP with multi-point NHS in a buffer solution (pH=8.0), the amino-containing PU films were added. After the reaction was run at room temperature for 0.5-1 h, the films were washed with distilled water several times prior to evaluation.

Article Example 27

Surface modification with PVP end-capped with NHS. To a container containing PVP end-capped with NHS in a buffer solution (pH=8.0), the amino-containing PU films were added. After the reaction was run at room temperature for 0.5-1 h, the films were washed with distilled water several times prior to evaluation.

Article Example 28

Multilayer coating through NHS-containing polymer and $NH_2$-containing polymer. The amino-containing polymer membrane synthesized in Example 19 was used to study the effect of coating via a layer by layer process. Briefly, the membrane disk containing amine functionality was soaked in PVP-NHS solution at pH=8.5. After 5 min, the disk was taken out and rinsed with DI-water, followed by soaking in PVP-NH$_2$ solution for 15 min. This process was repeated back and forth to achieve multi-layers of coating.

Example 29

Figure 1:
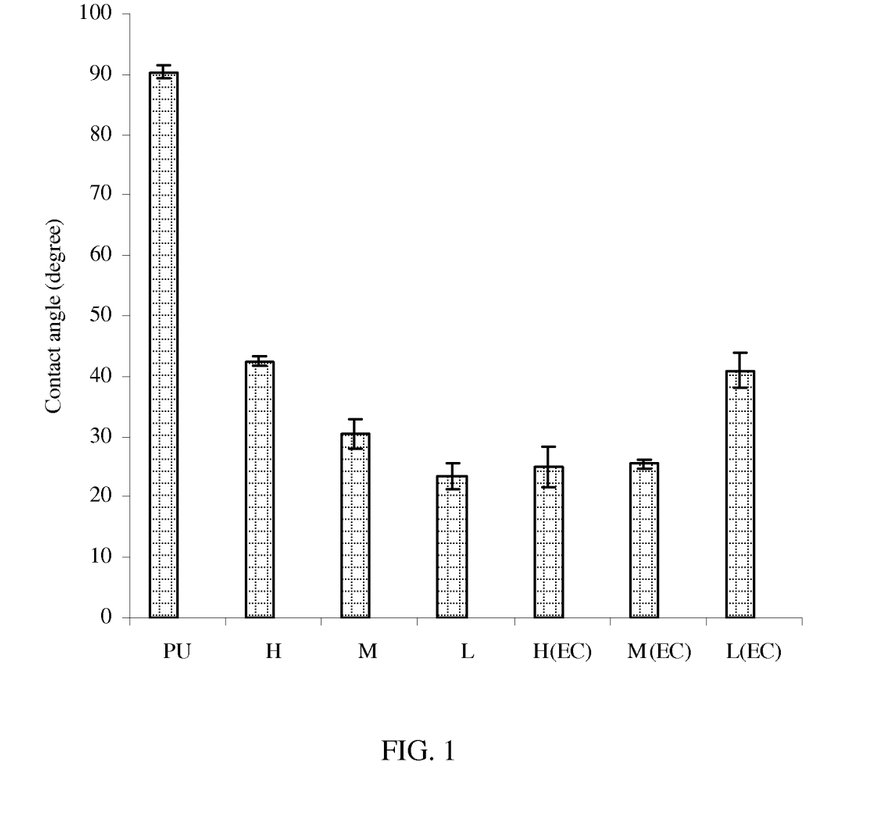
FIG. 1 shows the effect of PVP MW on contact angle of the modified PU-PVP surface: PU=polyurethane, H=high MW polymer, M=medium MW polymer, L=low MW polymer, each of which is prepared from multipoint PU coated with PVP/SE; H (EC)=high WM polymer, M (EC)=medium MW polymer, and L (EC)=low MW polymer, each of which is prepared from end-capped PU coated with PVP/SE. Without being bound by theory, it is believe herein that the multipoint PU coated with PVP/SE adopts a laid down orientation relative to the surface of the substrate, and the end-capped PU coated with PVP/SE adopts a tangential or perpendicular or grafted orientation relative to the surface of the substrate, as described herein.

Effects of polymer MW and concentration on contact angle of the amine or amino modified surface. To a container containing PVP with multi-point NHS in a buffer solution (pH=8.0), the amino-containing PU films were added. After the reaction was run at room temperature for 0.5-1 h, the films were washed with distilled water several times prior to evaluation. The effects of polymer MW and concentration (by weight) on contact angle of the amine or amino modified surface were studied. The results for the effects of polymer MW on contact angle are shown in FIG. 1.

Example 30

The measured MW (both weight and number average MW) of the polymers synthesized in some examples are shown in Table 2.

TABLE 2

MW[1] of the synthesized polymers shown in some examples

| Polymer[2] | $M_w$ (Daltons × $10^{-3}$) | $M_n$ (Daltons × $10^{-3}$) |
|---|---|---|
| Example 4 | 270.2 | 22.5 |
| Example 5 | 110.8 | 10.1 |
| Example 6 | 38.3 | 4.2 |
| H in Example 27 | 180.6 | 17.2 |
| M in Example 27 | 120.3 | 10.4 |
| L in Example 27 | 87.2 | 9.1 |
| H (EC) in Example 27 | 46.1 | 5.4 |
| M (EC) in Example 27 | 39.2 | 4.6 |
| L (EC) in Example 27 | 21.5 | 2.9 |

[1]MW of the polymers were measured by gel permeation chromatography (GPC);
[2]Polymers were shown in various examples.

Example 31

Figure 2:
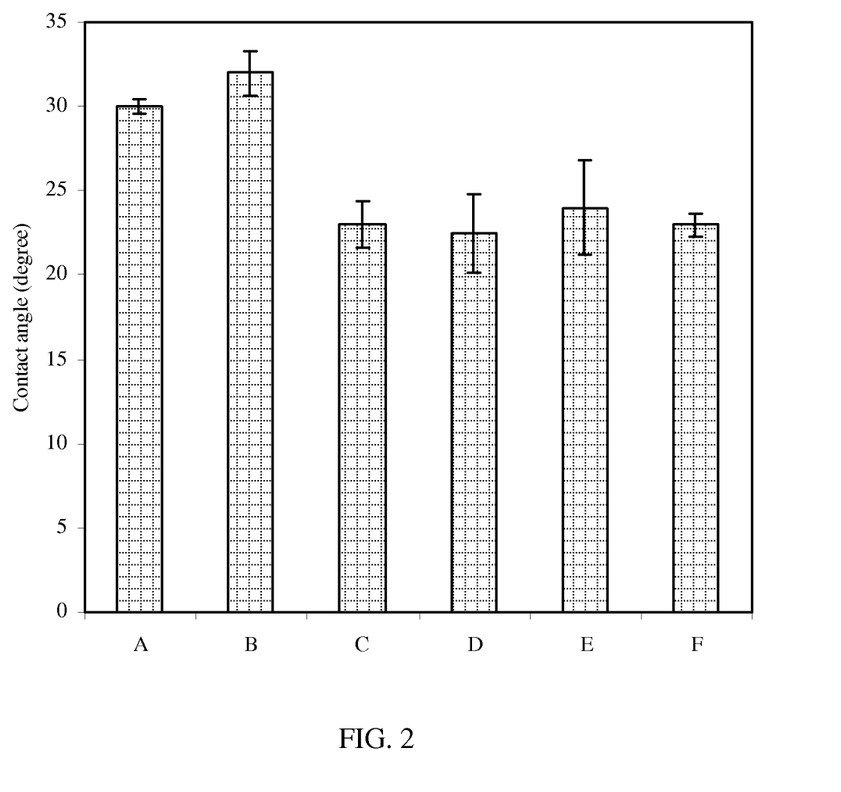
FIG. 2 shows the effect of physical coating stability with PVP: A=PVP-SE coating at RT (2 h); B=surface coated with PVP-SE conditioned in DI water at 100° C. for 2 h; C=surface coated with 3 times of 1% PVP (commercial); D=surface coated with 3 times of 1% PVP (commercial) conditioned in DI water at 37° C. for 24 h; E=surface coated with 3 times of 1% PVP (commercial) conditioned in DI water at 100° C. for 2 h; E=surface coated with 3 times of 1% PVP (commercial) conditioned in DI water at 100° C. for 24 h.

Stability of the polymer on the surface. To a container containing PVP with multi-point NHS in a buffer solution (pH=8.0), the amino-containing PU films were added. After the reaction was run at room temperature for 0.5-1 h, the films were washed with distilled water several times prior to evaluation. The stability of the polymer on the modified surface with changing temperature was studied and the result is shown in FIG. 2.

Example 32

Figure 3:
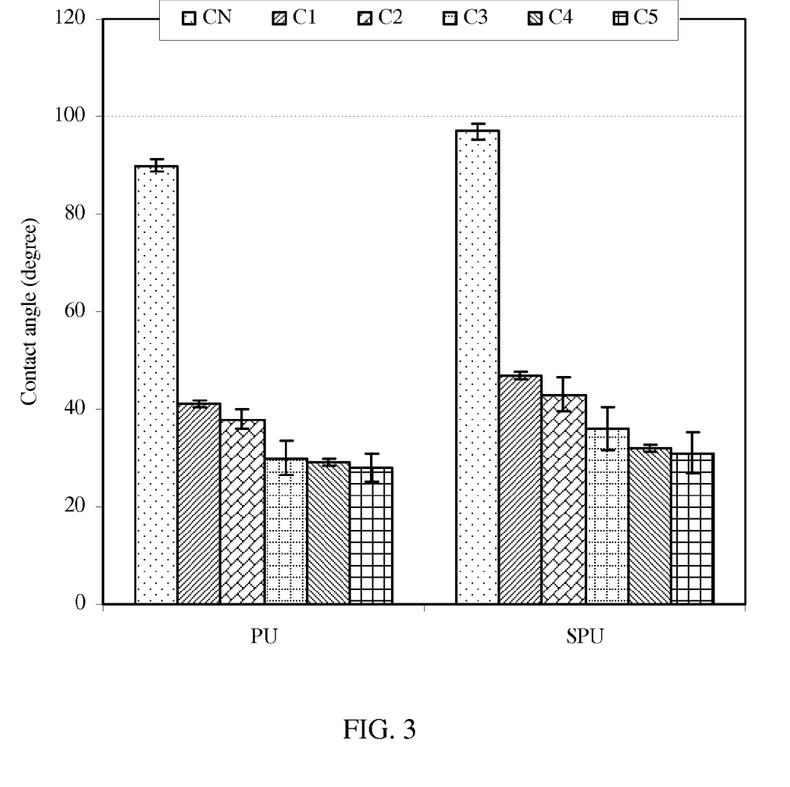
FIG. 3 shows the effect of coating times of the functional PVP-NHS polymer or multiple coating of PVP on contact angle of both PU and SPU: CN, C1, C2, C3, C4 and C5=no coating, 1st coating with PVP-NHS, $2^{nd}$ coating of PVP-NH$_2$, $3^{rd}$ coating with PVP-NHS, $4^{th}$ coating with PVP-NH$_2$ and $5^{th}$ coating with PVP-NHS; The coating was conducted at pH=8-8.5 and RT. 5 min for PVP-NHS and 15 min for PVP-NH$_2$ coating.

Effect of multilayer coating on contact angle of the polymer surface. The effects of multilayer coating of PVP on contact angle of PU and SPU surfaces were evaluated and shown in FIG. 3. The result shows that the modified surfaces showed improved wettability by reduced contact angle.

Example 33

Comparison between functional PVP with multi-point NHS and pre-crosslinked PVP with multi-point NHS. Table 3 shows the comparison of gel formation, solution turbidity and measured contact angle between non-pre-crosslinked and pre-crosslinked PVP-NHS polymers. The result shows that the modified surfaces showed improved wettability by reduced contact angle.

TABLE 3

Comparison between non-pre-crosslinked and pre-crosslinked PVP-NHS

| Material(a) | Gel formation(b) | Solution turbidity(c) | Contact angle |
|---|---|---|---|
| Control | − | +++ | 41.5 |
| #1 | − | ++ | 38.5 |
| #2 | − | + | 33.4 |
| #3 | − | +− | 31.2 |
| #4 | − | +− | 31.8 |
| #5 | + | N/A | N/A |

(a)Control, #1, #2, #3, #4 and 5# corresponds to non-pre-crosslinked PVP with multi-point NHS, pre-crosslinked PVP with multi-point NHS at 0.05%, 0.5%, 1.0%, 2%, 8% (by mole) of hexamethylenediamine, respectively.
(b)Gel formation (+ = yes and − = no) was observed by vision and filtration during and after synthesis.
(c) Solution turbidity (+ = yes, − = no and N/A = not available) was observed in polymer-containing aqueous solution at pH = 8.0. Polymer was coated on PU-NH2 surface.

Example 34

Figure 4:
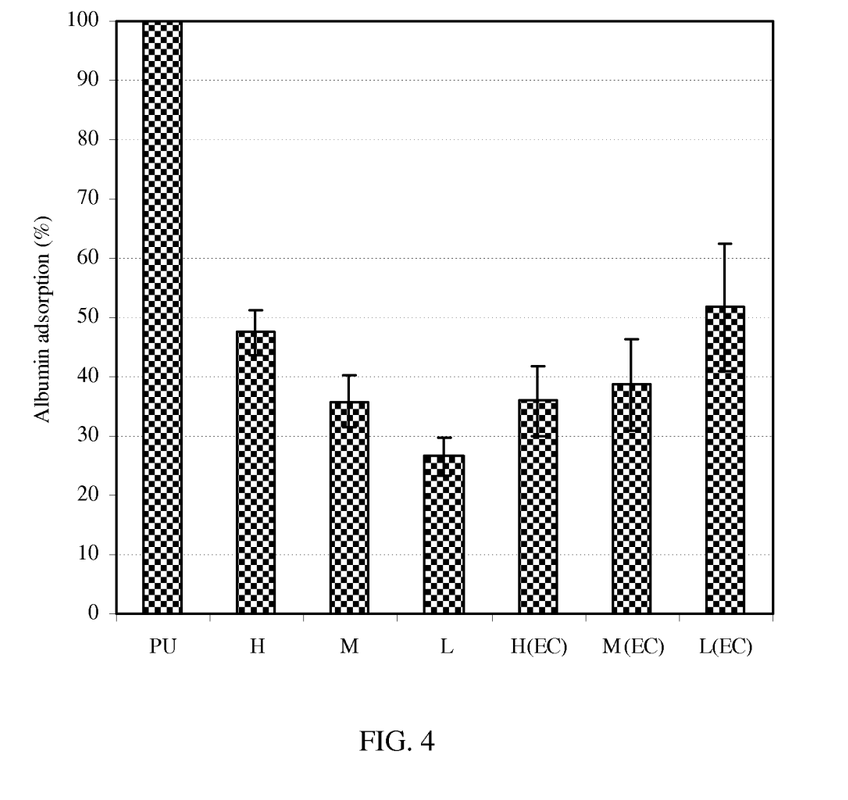
FIG. 4 shows the effect of PVP MW on human albumin adsorption onto the modified surface

Effect of polymer MW on human albumin adsorption onto the modified surface. The effect of polymer MW on human albumin adsorption onto the modified surface was evaluated and shown in FIG. 4. The result shows that all the modified surfaces showed significantly reduced protein adsorption values, as compared to original PU.

Example 35

Evaluation of other polymers. Table 4 shows the contact angle and human albumin adsorption values of the modified surface with other polymers. The result shows that all the modified surfaces including PEG with MW of 3,000, 6,000, 10,000 and 20,000 and poly(VP-co-MPC-co-AANHS) showed significantly reduced contact angle and protein adsorption values, as compared to original PU and SPU.

TABLE 4

Properties of PU and modified PU surfaces

| Material[1] | Contact angle (degree) | Albumin adsorption (%) |
|---|---|---|
| PU and surface modified with polymers | | |
| PU | 91.2 (2.3) | 100 |
| PEG3K | 64.0 (1.4) | 56.2 (0.4) |
| PEG6K | 42.1 (2.9) | 52.3 (2.3) |
| PEG10K | 38.5 (2.1) | 49.2 (3.5) |
| PEG20K | 46.0 (1.4) | 48.3 (0.9) |
| P(VP-PC) | 39.8 (6.0) | 42.8 (0.3) |
| SPU and surface modified with polymers | | |
| SPU | 98.3 (0.9) | 100 |
| PEG3K | 49.0 (2.8) | 49.3 (1.6) |
| PEG6K | 48.5 (6.4) | 48.2 (3.4) |
| PEG10K | 52.0 (4.2) | 42.3 (5.2) |
| PEG 0K | 49.3 (1.4) | 39.2 (1.2) |
| P(VP-PC) | 43.6 (5.3) | 39.8 (5.1) |

[1]PU = polyurethane, SPU = silicone polyurethane, PEG3K = poly(ethylene glycol) with MW = 3,000, and P(VP-PC) is the polymer containing both N-vinylpyrrolidone and phosphocoline.

Example 36

The surface functional groups of the modified PU films were identified by Fourier transform-infrared (FT-IR) spectroscopy and showed the expected diagnostic peaks.

Example 37

Photographs were taken for the contact angles of the surfaces with different materials. Significant water spreading was observed with both modified surfaces (PVP-modified surface and poly(VP-PC)-modified surface, as compared to original PU.

What is claimed is:

1. An article for use as a biological implant or prosthetic, the article comprising a substrate, and a grafted coating polymer covalently attached to the substrate through a reactive group selected from the group consisting of OH, NHS, HOBt, $NH_2$, $CO_2H$, CHO, SH and epoxide, and combinations thereof; wherein the grafted coating polymer comprises a copolymer of (a) (N-vinylpyrrolidone), (N,N-dimethylacrylamide), (N-methyl-N-vinylacetamide), (N-vinylformamide), (ethylene glycol), (methacryloyl phosphorylcholine), or (ethylene oxide), or a combination thereof; and (b) PEG acrylate, PEG methacrylate, (vinyl alcohol), (acrylic acid), (acrylic acid) sodium salt, or (acrylic acid) potassium salt, acrylic acid N-hydroxysuccinimide ester, alginic acid, hyaluronic acid, or a combination thereof, and wherein the grafted coating polymer is capable of resisting cell adhesion, protein deposition, or a combination thereof.

2. A process for manufacturing an article for use as an implant or prosthetic, the process comprising the step of contacting a substrate with a solution of a coating polymer under conditions where the coating polymer will covalently bond to the substrate through a reactive group selected from the group consisting of OH, NHS, HOBt, $NH_2$, $CO_2H$, CHO, SH and epoxide, and combinations thereof.

3. A process for manufacturing an article for use as an implant or prosthetic, the process comprising the steps of:
(a) contacting a substrate having a reactive group selected from the group consisting of OH, NHS, HOBt, $NH_2$, $CO_2H$, CHO, SH and epoxide, and combinations thereof, with a solution of a coating polymer under conditions where the coating polymer will covalently bond to the substrate to form a first coated substrate;
(b) contacting the first coated substrate from (a) with a solution of a coating polymer under conditions where the coating polymer will covalently bond to the first coated substrate to form a second coated substrate;
(c) contacting the second coated substrate from (b) with a solution of a coating polymer under conditions where the coating polymer will covalently bond to the second coated substrate to form a third coated substrate; and
(d) optionally repeating step (c) 1 to 5 times.

4. The article of claim 1 wherein the substrate forms the basic structure of the implant or prosthetic.

5. The article of claim 1 wherein the substrate is a polymer.

6. The article of claim 1 wherein the substrate comprises a polyurethane (PU), a silicone polyether urethane (SPU), a polyacrylate, or a copolymer thereof.

7. The article of claim 1 wherein the substrate comprises a polyacrylate comprising a copolymer of methyl methacrylate and one or more amino-containing monomers selected from N-amino-poly(ethylene glycol) acrylamide, N-amino-poly(ethylene glycol) methacrylamide, N-amino-siloxane-containing acrylamide, N-amino-siloxane-containing methacrylamide, N-amino-alkyl(aryl) acrylamide, N-amino-alkyl (aryl) methacrylamide, and combinations thereof.

8. The article of claim 1 wherein the substrate comprises a cross-linked polymer network of one or more amino-containing monomers selected from N-amino-poly(ethylene glycol) acrylamides, N-amino-siloxane-containing acrylamides, N-amino-alkyl(aryl) acrylamides, and combinations thereof.

9. The article of claim 1 wherein the grafted coating polymer comprises a copolymer selected from the group consisting of poly(N-vinylpyrrolidone-acrylic acid), poly (VP-AA-AANHS), poly(VP-DMAm-co-AANHS), poly (VP-MVAm-AANHS), poly(DMAm-MVAm-AANHS), and poly(VP-MPC-AANHS), or salt of any of the foregoing, and combinations thereof.

10. The article of claim 1 wherein the grafted coating polymer comprises a copolymer selected from the group consisting of poly(VP-AA), poly(VP-DMAm-AA), poly (VP-MVAm-AA), poly(DMAm-MVAm-AA), poly(VP-MPC-AA), or salt of any of the foregoing, and combinations thereof; where at least a portion of the acrylic acid monomers are activated esters.

11. The article of claim 1 wherein the grafted coating polymer comprises a copolymer selected from the group consisting of poly(VP-AANHS), poly(VP-DMAm-AANHS), poly(VP-MVAm-AANHS), poly(DMAm-MVAm-AANHS), poly(VP-MPC-AANHS).

12. The article of claim 1 wherein the grafted coating polymer is a cross-linked water soluble polymer.

13. The article of claim 1 wherein the grafted coating polymer is an amide cross-linked water soluble polymer.

14. The article of claim 1 wherein the implant or prosthesis is a stent.

15. The article of claim 1 wherein the implant or prosthesis is a contact lens.

16. The article of claim 1 wherein the implant or prosthesis is an intraocular lens.

* * * * *